United States Patent
Istoc

(10) Patent No.: US 10,532,156 B2
(45) Date of Patent: **\*Jan. 14, 2020**

(54) GEOFENCING FOR MEDICAL DEVICES

(71) Applicant: Medtronic MiniMed, Inc., Northridge, CA (US)

(72) Inventor: Emilian Istoc, Winnetka, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 15/632,102

(22) Filed: Jun. 23, 2017

(65) Prior Publication Data

US 2017/0290978 A1    Oct. 12, 2017

Related U.S. Application Data

(63) Continuation of application No. 14/463,600, filed on Aug. 19, 2014, now Pat. No. 9,717,845.

(51) Int. Cl.
| | | |
|---|---|---|
| *A61M 37/00* | (2006.01) | |
| *A61M 5/172* | (2006.01) | |
| *A61M 5/142* | (2006.01) | |
| *G16H 40/40* | (2018.01) | |
| *G06F 19/00* | (2018.01) | |

(52) U.S. Cl.
CPC ............ *A61M 5/172* (2013.01); *A61M 5/142* (2013.01); *A61M 5/1723* (2013.01); *G06F 19/00* (2013.01); *G06F 19/3468* (2013.01); *G16H 40/40* (2018.01); *A61M 2005/14208* (2013.01); *A61M 2205/18* (2013.01); *A61M 2205/3553* (2013.01); *A61M 2205/3561* (2013.01); *A61M 2205/3569* (2013.01); *A61M 2205/3584* (2013.01); *A61M 2205/505* (2013.01); *A61M 2205/52* (2013.01); *A61M 2205/581* (2013.01); *A61M 2205/6009* (2013.01); *A61M 2230/201* (2013.01)

(58) Field of Classification Search
CPC ............ A61M 2205/52; A61M 5/1723; A61M 2205/3584; A61M 2005/14208; A61M 2205/50; G06F 19/3468; G06F 19/3412; A61B 5/1112

See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |

(Continued)

*Primary Examiner* — Emily L Schmidt

(57) ABSTRACT

A medical therapy system for delivering at least two therapies based on a geographic location of the medical therapy system is disclosed. The medical therapy system includes an infusion pump having a case that contains a processor, memory, a drive mechanism, a reservoir, a radio, and a sensor suite. The sensor suite includes a global positioning system (GPS) receiver to determine a location of the infusion pump. The processor receives the location of the infusion pump and executes first instructions stored in the memory. The processor executes second instructions stored in the memory only when the location of the infusion pump is within a safe zone defined around specified GPS coordinates.

20 Claims, 7 Drawing Sheets

(56) References Cited

U.S. PATENT DOCUMENTS

| | | |
|---|---|---|
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |

GEOFENCING FOR MEDICAL DEVICES

CROSS REFERENCE TO RELATED APPLICATIONS

The present disclosure is a Continuation of U.S. patent application Ser. No. 14/463,600, filed on Aug. 19, 2014, the contents of which are hereby incorporated by reference in their entirety.

FIELD OF THE INVENTION

This invention relates to infusion systems with and without a sensor to provide feedback regarding a characteristic of a body.

BACKGROUND OF THE INVENTION

Diabetes is a disease in which the body does not produce or properly use insulin. Approximately 13 million people in the United States have been diagnosed with some form of diabetes. Type 1 diabetes results from the body's failure to produce insulin. Type 2 diabetes results from insulin resistance in which the body fails to properly use insulin. To effectively manage the disease, diabetics must closely monitor and manage their blood glucose levels through exercise, diet and medication. In particular, both Type 1 and Type 2 diabetics rely on insulin delivery to control their diabetes. Traditionally, insulin has been injected with a syringe multiple times during the day, usually self-administered by the diabetic. In recent years, external infusion pump therapy has been increasing, especially for delivering insulin to diabetics using devices worn on a belt, in a pocket, or the like, with the insulin delivered from a reservoir via a catheter with a percutaneous needle or cannula placed in the subcutaneous tissue.

External infusion devices allow Type 1 and Type 2 diabetics to better manage and control their diabetes. The external infusion device is intended to be used continuously and delivers insulin twenty-four hours a day according to a programmed plan unique to each pump wearer. A small amount of insulin, or a basal rate, is given continually. This insulin keeps the user's blood glucose levels in the desired range between meals and overnight. When food is eaten, the user programs the external infusion device to deliver a bolus of insulin matched to the amount of food that will be consumed. The user determines how much insulin will be given based on factors including insulin sensitivity, insulin duration, insulin-on-board, and the like. In many instances, external infusion devices include a processor that assists the user in making therapy decisions based on information provided by the user including blood glucose levels, carbohydrate intake, and/or information from the external infusion device. Exemplary devices are described in U.S. Pat. No. 6,554,798 issued on Apr. 29, 2003 to Mann et al., and entitled "External Infusion Device with Remote Programming, Bolus Estimator and/or Vibration Alarm Capabilities," which is specifically incorporated by reference herein.

Automating or partially automating programming for the infusion device can help simplify and improve therapy. Knowing a user's location can enable partial or full automation of specific aspects of infusion device therapy. Accordingly, it can be beneficial to enable GPS receiver data to be integrated into infusion therapy.

SUMMARY OF THE DISCLOSURE

In one embodiment a medical therapy system for both approved and trial therapies is disclosed. The medical therapy system includes an infusion pump with a case containing a processor, memory, a drive mechanism, a reservoir, communication hardware and a sensor suite. The sensor suite includes a global positioning system (GPS) receiver to determine GPS coordinates of the infusion pump. The GPS receiver is coupled to the processor which executes first instructions corresponding to an approved therapy stored in the memory. The processor executes second instructions corresponding to a trial therapy stored in the memory when the location of the infusion pump is within a safe zone defined around specified GPS coordinates.

In another embodiment a medical therapy system for delivering at least two therapies based on a geographic location of the medical therapy system is disclosed. The medical therapy system includes an infusion pump with a case containing a processor, memory, a drive mechanism, a reservoir, a radio and a sensor suite. The system further includes an infusion pump controller that has a sensor suite having a global positioning system (GPS) receiver. The controller further including a controller processor, controller memory and controller radio that enables bi-directional communication with the radio associated with the infusion pump. The GPS receiver works with the controller processor and controller radio to send instructions to the infusion pump to execute first instructions stored in the memory. The controller instructing the infusion pump to execute second instructions stored in the memory when the location of the controller is within a safe zone defined around specified GPS coordinates.

In still another embodiment a medical therapy system for delivering at least two therapies based on a geographic location of the medical therapy system is disclosed. The medical therapy system includes an infusion pump having a case that contains a processor, memory, a drive mechanism, a reservoir, a radio, and a sensor suite. The sensor suite includes a global positioning system (GPS) receiver to determine a location of the infusion pump. The processor receives the location of the infusion pump and executes first instructions stored in the memory. The processor executes second instructions stored in the memory only when the location of the infusion pump is within a safe zone defined around specified GPS coordinates.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION

Figure 1:
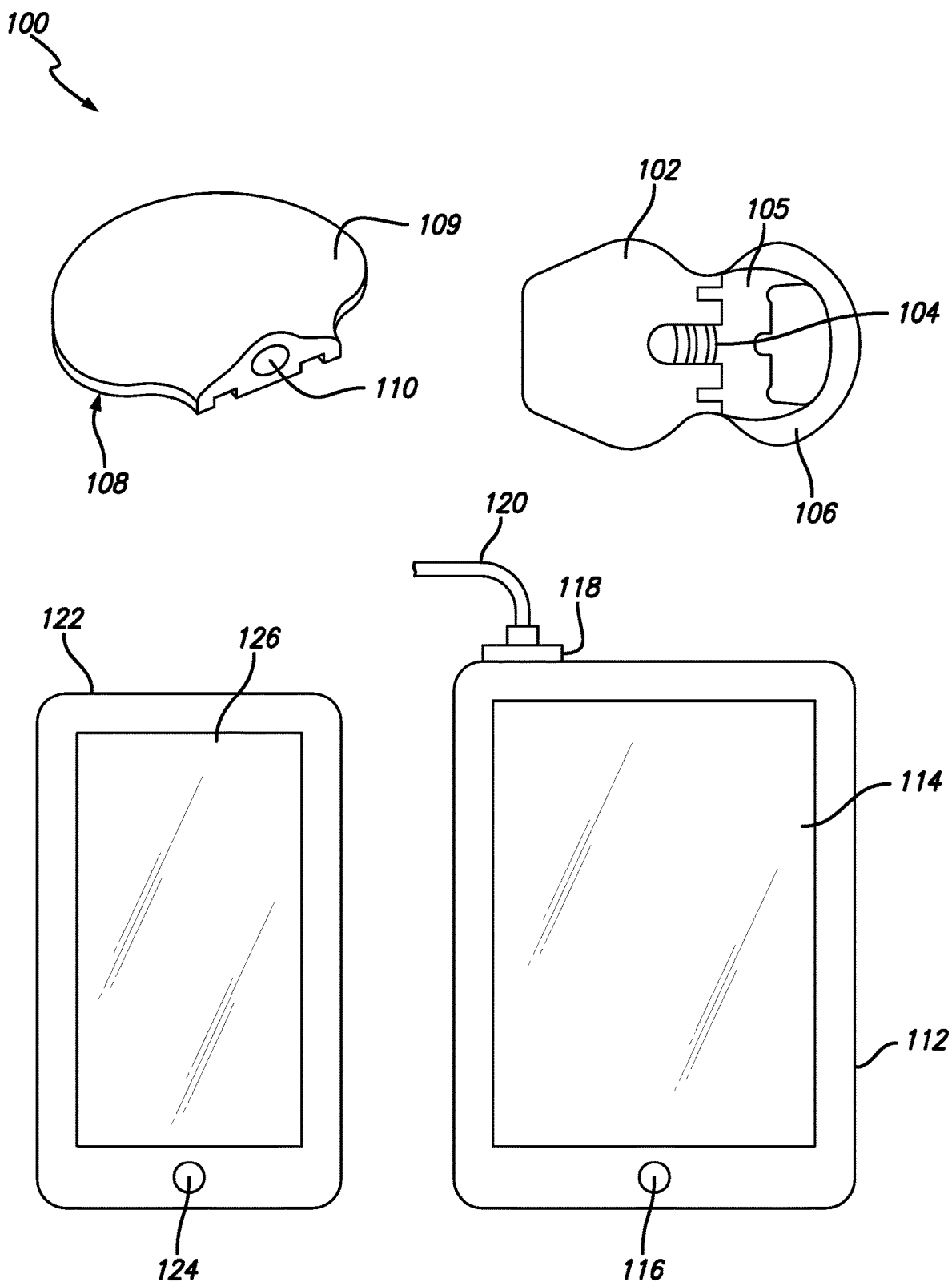
FIG. 1 is an exemplary illustration of components within an infusion system, in accordance with embodiments of the present invention.

As shown in the drawings for purposes of illustration, the invention is embodied as a portable infusion system with an optional sensor set that provides continuous data of the sensor readings to the infusion system. In some embodiments a wireless controller having a touchscreen user interface and integrated GPS receiver is used to control an infusion pump having minimal or no user interface. In other embodiments, the infusion pump itself includes a GPS receiver and a user interface with a touchscreen. In still other embodiments both a wireless controller and an infusion pump include a GPS receiver and a user interface. In every embodiment, enabling the GPS receiver allows the infusion pump and controller to enable or disable various functions of the infusion system depending on the location of a user. Because commercial GPS provides a "worst case" pseudo-range accuracy of 7.8 meters at a 95% confidence level, the GPS enabled infusion system includes a user defined safe zone specified around particular GPS coordinates. Accordingly, in some embodiments an infusion pump may have multiple operating instructions stored in memory than are automatically or manually activated when a user enters a designated safe zone. The various operating instructions can enable the infusion pump to vary therapy protocols or automatically enable or disable infusion system features, options and controls.

Thus, a GPS receiver enabled infusion system can enable simplification of therapy for users participating in clinical trials along with providing automatic or user controlled enhancements to infusion therapy. In embodiments of the present invention, the analyte sensor set and infusion system are for determining glucose levels in the blood and/or bodily fluids of the user without the use of, or necessity of, complicated monitoring systems that require user training and interaction. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the infusion system may also include the capability to be programmed to record optional sensor data at specified time intervals. The infusion system and analyte sensor are primarily adapted for use in subcutaneous human tissue. However, still further embodiments may be placed in other types of tissue, such as muscle, lymph, organ tissue, veins, arteries or the like, and used in animal tissue. The analyte sensors may be subcutaneous sensors, transcutaneous sensors, percutaneous sensors, sub-dermal sensors, skin surface sensors, or the like. Embodiments may measure and record sensor readings on an intermittent or continuous basis.

FIG. 1 is an exemplary illustration of components within an infusion system 100, in accordance with embodiments of the present invention. The sensor 102 is shown from an exemplary top view as if it has been inserted into a patient. In one embodiment the sensor 102 utilizes an electrode-type sensor while in alternative embodiments, the sensor 102 may use other types of sensors, such as chemical based, optical based or the like. In further alternate embodiments, the sensor 102 may be of a type that is used on the external surface of the skin or placed below the skin layer of the user or placed in the blood stream of the user. Other embodiments of a surface mounted sensor would utilize interstitial fluid harvested from the skin.

In some embodiments, the sensor 102 is an assembly commonly known as a "sensor set" that includes, but it not limited to the connector 104, sensor adhesive (not shown) covered by an adhesive backing 106, an introducer needle (not shown in FIG. 1), a sensing portion of the sensor to be placed in a body (not shown), and a mounting base 105. In one embodiment the connector 104 is integrally injection molded from plastic with the mounting base 105. The connector 104 further includes electrical contacts that interface with contacts on the sensor. On a side opposite that is shown in FIG. 1, the adhesive is applied to the mounting base 105 and the adhesive backing 116 is further applied over the adhesive.

An electronic package 108 is also included in the infusion system 100. The electronics package 108 includes a package housing 109 with a package port 110. The package port 110 is designed to couple with the electrical contact on the connector 104 thereby providing power and other electrical interfaces between the electronics package 108 and the sensor 102. In one embodiment the electronics package further includes a power source, processor and transmitter within the package housing 109. The power source provides power for the processor and transmitter and when coupled to the connector 104, further powers the sensor 102. In such an embodiment signals generated by an installed sensor can be processed via the processor and transmitted to another device such as, but not limited to infusion pump 112. In other embodiments, the electronics package 108 includes at least a power source, processor, transmitter along with memory and a receiver. In these embodiments sensor signals from an installed sensor can be stored to memory within the package housing 109 and periodically transmitted to the infusion pump 112 or other devices configured to communicate with the electronics package 108. Additionally, the inclusion of the receiver within the electronics package 108 would enable two-way communication between other devices and the electronics package 108.

The inclusion of memory within the electronics package 108 can enable the combined electronics package 108 and sensor 102 to be used as a Holter-type recording device that can use the package port 110 to interface with either the sensor 102 or a docking station (not shown) that is further connected to a computer of tablet computing device. When used as a recording device the combined electronics package 108 and sensor 102 have the capability to record and store data as it is received from the sensor 102. When the electronics package 108 is coupled to a docking station the data stored on the memory of the electronics package 108 can be transferred to networked or local data storage and analyzed using general computing processors such as desktops, laptops, notebooks, netbooks, tablets, or handheld computing devices such as, but not limited to smart phones and the like. To enable data transfer through the dock, the dock may further include a data transfer cable such as, but not limited to USB or Thunderbolt or Ethernet directly coupled to a computing device.

The infusion pump 112 included in the infusion system 100 includes a tubing 120 that is in connected to a reservoir 118 within the infusion pump 112. Other characteristics of the infusion pump include a display 114 and a user interface 116. In some embodiments the display 114 is a touchscreen thereby making the display 114 an integrated component of the user interface 116. The infusion pump 112 can further include a radio transmitter and receiver that enables wireless communication. In some embodiments the radio transmitter is a BLUETOOTH radio that includes the BLUETOOTH LOW ENEGRY profile. In other embodiments a custom secure radio transmission system or protocol is used. The radio transmitter within the infusion pump 112 enables wireless transmission with the electronics package 108 thereby allowing sensor data to processed and analyzed by the infusion pump 112 along with showing sensor data on the display 114. In some embodiments there are multiple radio transmitters within the infusion pump 112 some of which are capable of transmitting and receiving data using at least one of the commercially available standards such as, but not limited to Long Term Evolution (LTE), GPRS, EDGE, EVDO, Wi-Fi, and the like.

In some embodiments a controller 122 having a controller display 126 and controller interface 124 is optional. In other embodiments the controller 122 may be required. An example of an embodiment where the controller 122 may be required is a system where the infusion pump 112 does not include a user interface or has a minimal or simplified user interface, such as but not limited to patch pump systems. In all embodiments, the controller display 126 can be a touch-screen enabling the controller display 126 and the controller interface 124 to function as a user interface to remotely control the infusion pump 112. The controller 122 includes a controller radio (not shown) that enables bi-directional communication between the controller 122 and the infusion pump 112. In some embodiments the controller radio uses the BLUETOOTH LOW ENERGY communication protocol to communicate with the infusion pump 112. In other embodiments a proprietary secure communication protocol is used between the controller 122 and the infusion pump 112. The controller radio can further enable communication between the controller 122 and the electronics package 108 associated with the sensor set. In one embodiment the controller 122 is a commercially available mobile phone configured to run proprietary or customized software capable of controlling the infusion pump 112. In other embodiments the controller 122 is a custom device specifically designed to control the infusion pump 112.

Transmission of sensor data to the infusion pump 112 further enables real-time glucose monitoring which can further enable low-glucose suspend functionality. In these embodiments if the sensor data indicates a blood sugar level below a specified threshold, the infusion pump 112 can suspend delivery of basal insulin. In some embodiments the raw sensor data measured by the sensor 102 is manipulated or processed using the processor within the electronics package 108 to determine sensor data from interstitial fluid that corresponds to a blood glucose level. In still other embodiments, the electronics package 108 transmits the raw sensor data to the insulin pump 112 where the raw sensor data is processed to correspond to a blood glucose level. In still other embodiments, the electronics package 108 transmits both the raw sensor data and a first calculated blood glucose level to the insulin pump. In these embodiments the insulin pump can then use a different algorithm to calculate a second blood glucose level from the raw sensor data. The second blood glucose level then being used in conjunction with the first blood glucose level to determine a third calculated blood glucose level.

Further description regarding the sensor and associated sensor set can be found in U.S. Pat. No. 6,248,067, entitled ANALYTE SENSOR AND HOLIER-TYPE MONITOR SYSTEM AND METHOD OF USING THE SAME, U.S. Pat. No. 5,586,553, entitled TRANSCUTANEOUS SENSOR INSERTION SET, and U.S. Pat. No. 5,594,643, entitled DISPOSABLE SENSOR INSERTION ASSEMBLY, all of which is herein incorporated by reference.

Figure 2A:
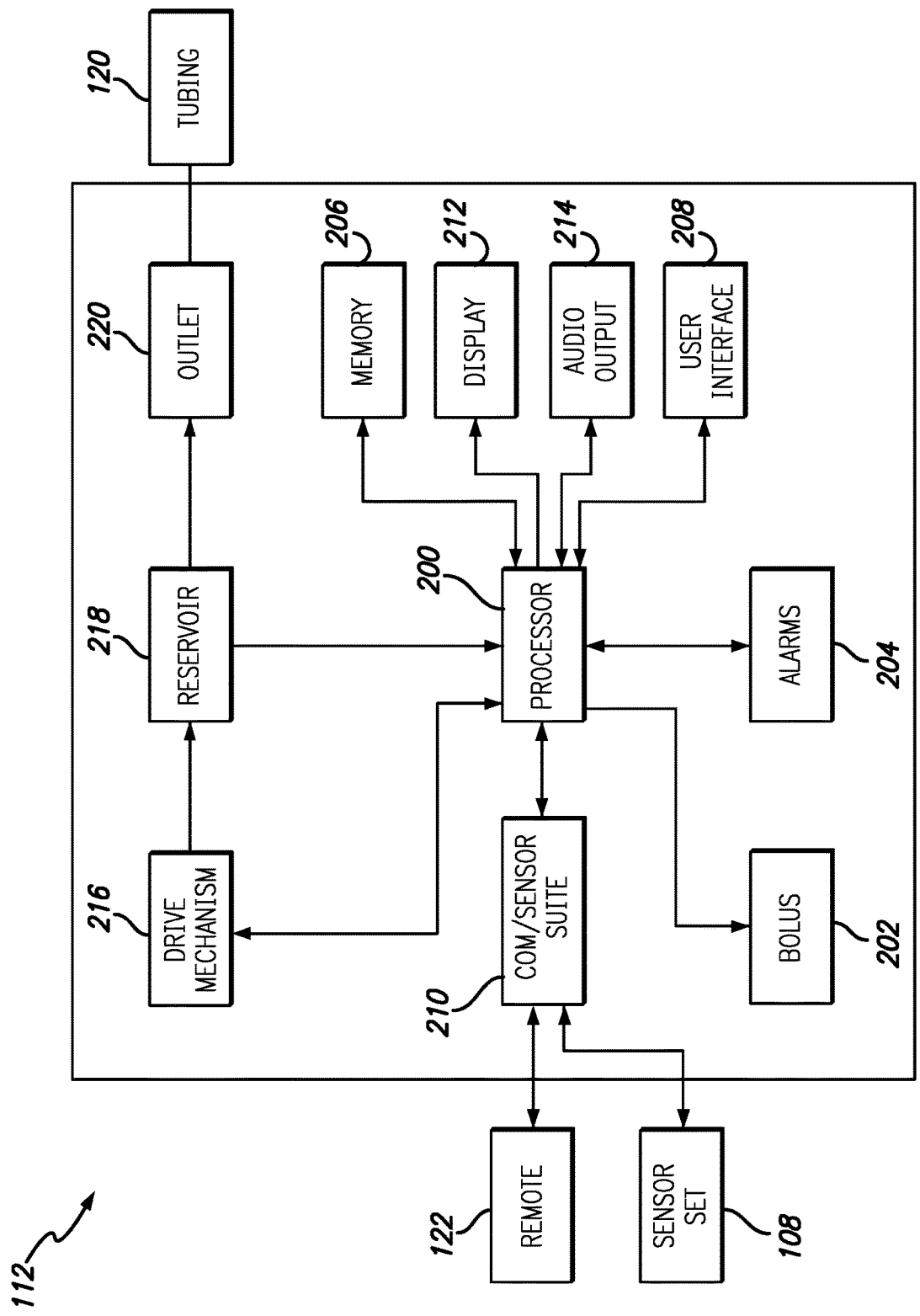
FIGS. 2A and 2B are block diagrams illustrating exemplary components within the infusion pump and the controller, in accordance with embodiments of the present invention.
Figure 2B:
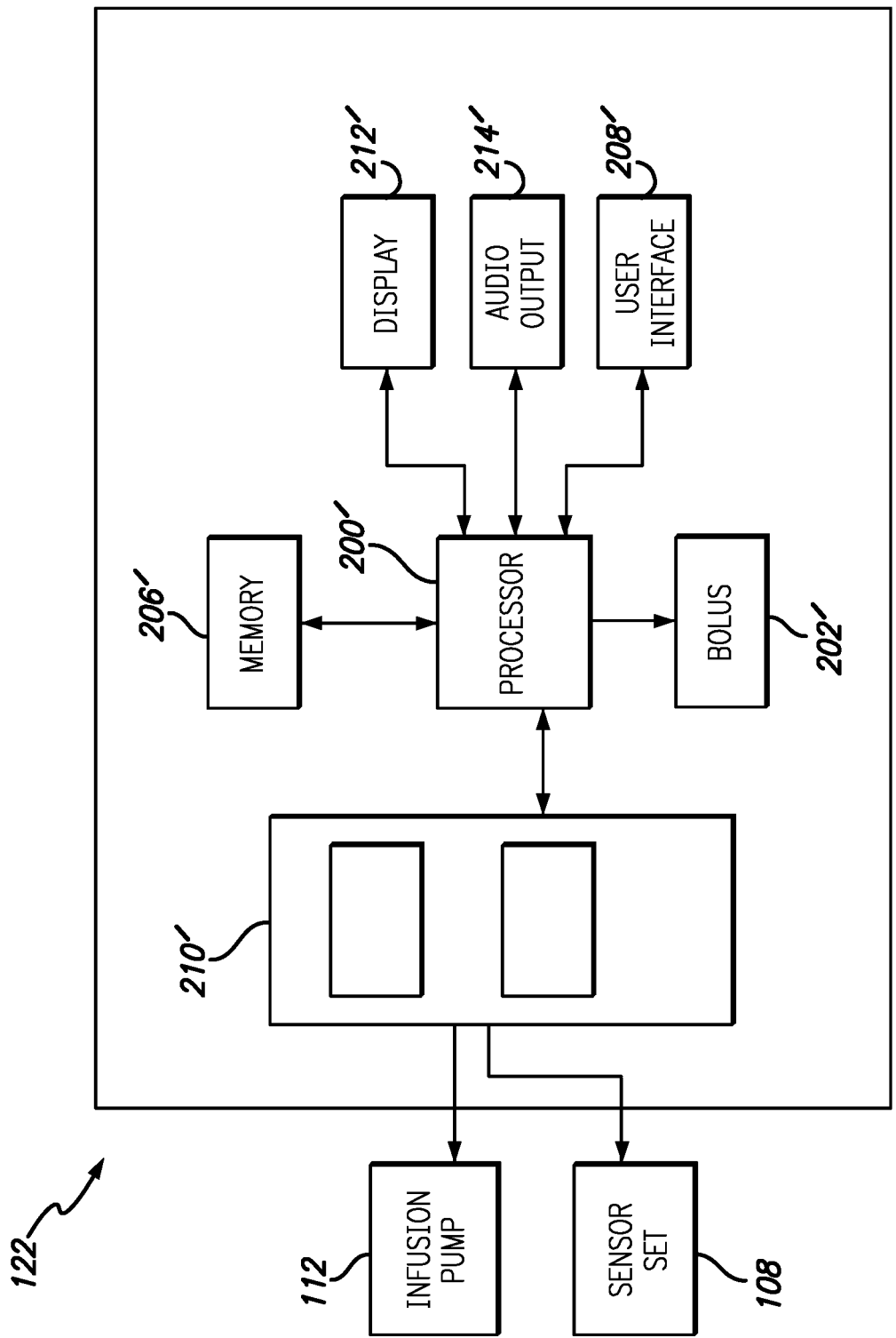

FIGS. 2A and 2B are block diagrams illustrating exemplary components within the infusion pump 112 and the controller 122, in accordance with embodiments of the present invention. The components or elements included in FIGS. 2A and 2B are intended to be illustrative of selected components and should not be construed as inclusive of all components within the infusion pump and controller. As illustrated in FIGS. 2A and 2B the infusion pump and controller share many common components. This is not be construed as the infusion pump and controller having identical components with identical part numbers. Rather, for simplicity, controller components that have analogue in the infusion pump will be designated with a "prime". These components are intended to perform similar or identical functions in the controller as the analogous part in the infusion pump. For example, the infusion pump 112 includes a processor 200 capable of executing program instructions that are stored in either memory integrated within the processor 200 or in a memory 206. Likewise, the controller 122 includes a processor 200' and a memory 206' that performs many, but not all of the same functions as the processor 200 and memory 206 in the infusion pump 112.

The program instructions executed by the processor 200 enable actuation of a drive mechanism 216 that is coupled to the processor. The drive mechanism 216 is further coupled to a reservoir 218 that contains a fluid to be infused into a user via outlet 220 and tubing 120. The infusion pump 112 further contains bolus functions as illustrated by bolus element 202 coupled with processor 200. Bolus element 202 can enable various types and profiles of bolus delivery from the infusion system 112. In some embodiments the bolus element 202 is optionally found in the controller 122 as bolus element 202'.

Further coupled to the processors 200/200' are an alarms component 204/204', a display 212/212', audio output 214/214' and a user interface 208/208'. Accessible via the user interface 208/208' and display 212/212', the alarms component 205/205' allows users to program various alarms conditions such as, but not limited to low or high level thresholds for sensor measurements, periodic alarms and the like. The alarms component 205/205' can use the display 212/212' and audio output 214/214' to draw the attention of a user regarding an alarm condition.

In some embodiments the alarm component 205/205' further includes a vibration alarm that enables vibration of the entire infusion pump 112, controller 122 or both so a user can be discretely notified of an alarm condition without the use of audio output 214/214'. In one embodiment audio output 214/214' in accomplished via a speaker within the case of the infusion pump. In other embodiments, a piezoelectric sound generator can be used to generate audio output 214/214'. Audio output 214/214' can be used to notify a user of an alarm condition and also to provide audio feedback regarding operation of the user interface.

The display 212/212' can show various information regarding the status of the infusion pump 112, the controller 122, both and/or an associated sensor, or the measurements from the sensor itself. Examples of infusion pump 112, controller 122 or sensor status that can be shown on the display 212/212' include, but are not limited to battery life, volume of fluid in the reservoir, connection status with the sensor, remaining sensor life, sensor hydration levels, sensor readiness and the like. The display 212/212' also displays real-time data from the sensor along with trend data based on sensor readings and user specified threshold values stored in the memory 206/206'. Via the user interface 208/208', the display 212/212' can be custom configured by a user to display particular information in a particular format. For example, in one embodiment the user can choose to have sensor data displayed as a moving line graph with a user defined number of previous samples used to determine trend data. In another embodiment, sensor data can be displayed as a bar graph or other graphical format. Other embodiments allow users to define fonts, font sizes, kerning, date format, clock format/size and the like.

The processor 200/200' within the infusion pump 112 or the controller 122 is further coupled to a communications and environmental sensor suite 210/210'. Within the communication and environmental sensor suite 210/210' are radios to enable secure wireless communications and environmental sensors such as, but not limited to accelerometers, ambient light sensors, global positioning satellite (GPS) receivers, microphones, clocks and compasses. The radios within the infusion pump 112 and controller 122 enable communication between the infusion pump 112, the controller 122 and the electronics package 108 associated with the sensor set.

The environmental sensors provide data to the processor within the infusion pump or controller regarding particular physical characteristics or environmental conditions around the infusion pump or controller. For example, inclusion of accelerometers enables the processor to determine the orientation of the infusion pump thereby automatically orienting pump information on the display to be easily readable by the user. Similarly ambient light sensors can enable the display to be brightened or dimmed automatically. Likewise, a microphone may detect ambient noise and automatically adjust audible alarms to appropriate levels. In other embodiments, data combinations from various sensors such clocks, ambient light sensors and microphones can be used to automatically determine audible alarm intensity. For example, if a clock indicates it is 3 AM, the ambient sensors determine it is dark, microphones detect very little ambient noise, and accelerometers indicate sporadic movement it may be determined the user is asleep and audible alarms may be automatically programmed to start off somewhat quietly and gradually increase in intensity over time.

In embodiments that include a GPS receiver, various functions of the infusion device can be automatically changed based on the location of the infusion device or infusion device and controller. For example, a first set of program instructions is used to operate the infusion system until the GPS receiver detects the controller or infusion device is within a specified distance of particular GPS coordinates. Upon being within the specified distance, or "safe zone" of the particular GPS coordinates, a second set of instructions can be used to operate the infusion system. In other embodiments, a user may receive a prompt on either the controller or the infusion pump to manually activate features enabled by the second set of instructions based on the location reported by the integrated GPS receiver. Due to geographic, architectural or physical limitation it may be necessary to use an amplified or active indoor/outdoor GPS antenna or repeater to ensure a GPS signal can be received within the safe zone. The use of GPS as an acronym for Global Positioning System should not be construed as limiting the disclosure to receivers using signals from GPS satellites. Other satellite based positioning/navigation systems such as, but not limited to GLONASS, Galileo, Beidou, COMPASS, IRNSS, and QZSS should be considered to fall within the scope of this disclosure. Additionally, while GPS signals may be used to determine a location of a user other techniques such as, but not limited to databases correlating Wi-Fi signals to locations can also be used. In one embodiment Wi-Fi signals are used to supplement GPS signal data to provide enhanced location resolution in urban areas. In still other embodiments, Wi-Fi signals alone are used to determine the location of a user.

Figure 3A:
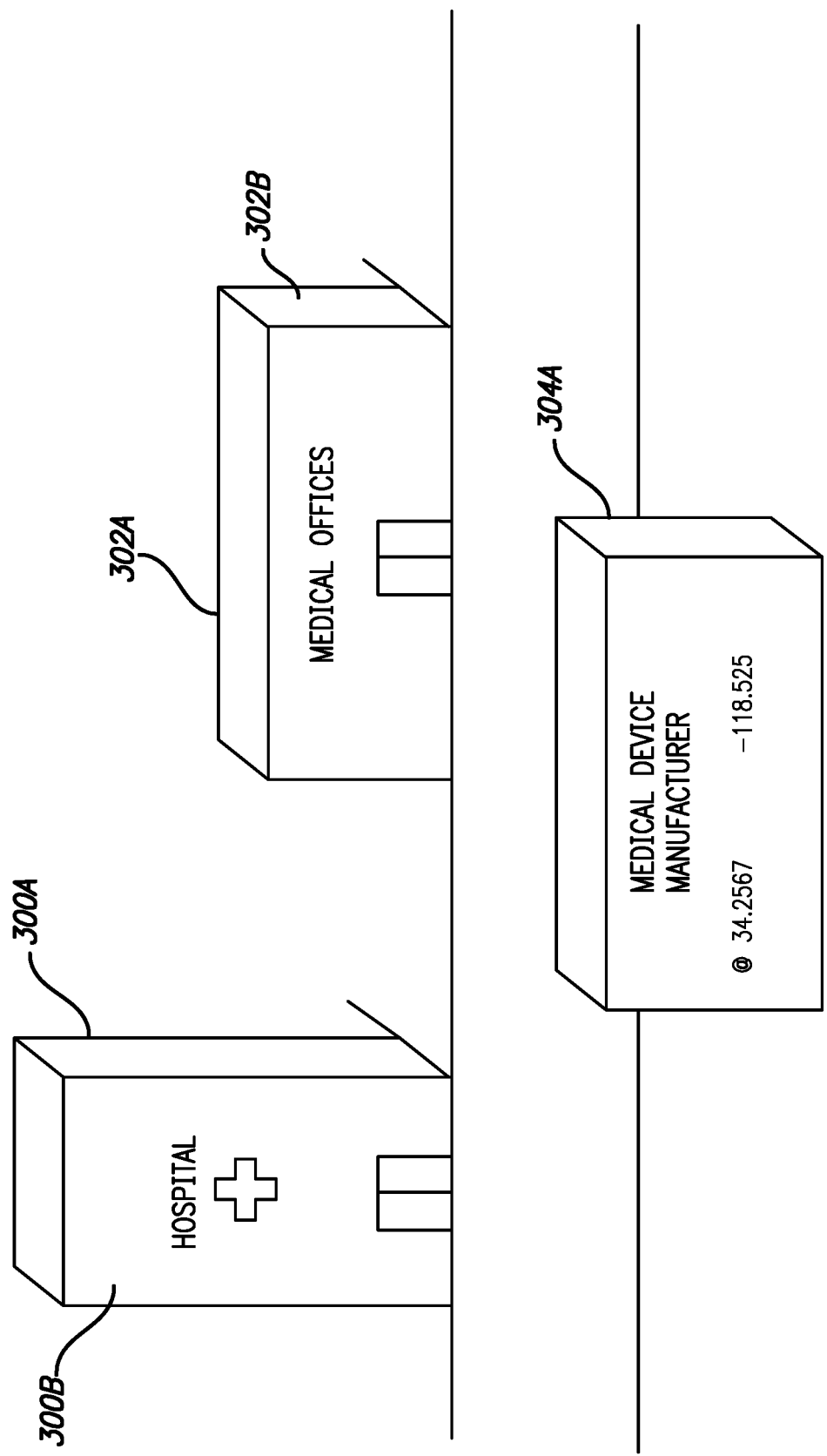
FIGS. 3A and 3B are exemplary illustrations of various locations or scenarios where inclusion of a GPS receiver could be used to enable or disable various features of the infusion pump, in accordance with embodiments of the present invention.
Figure 3B:
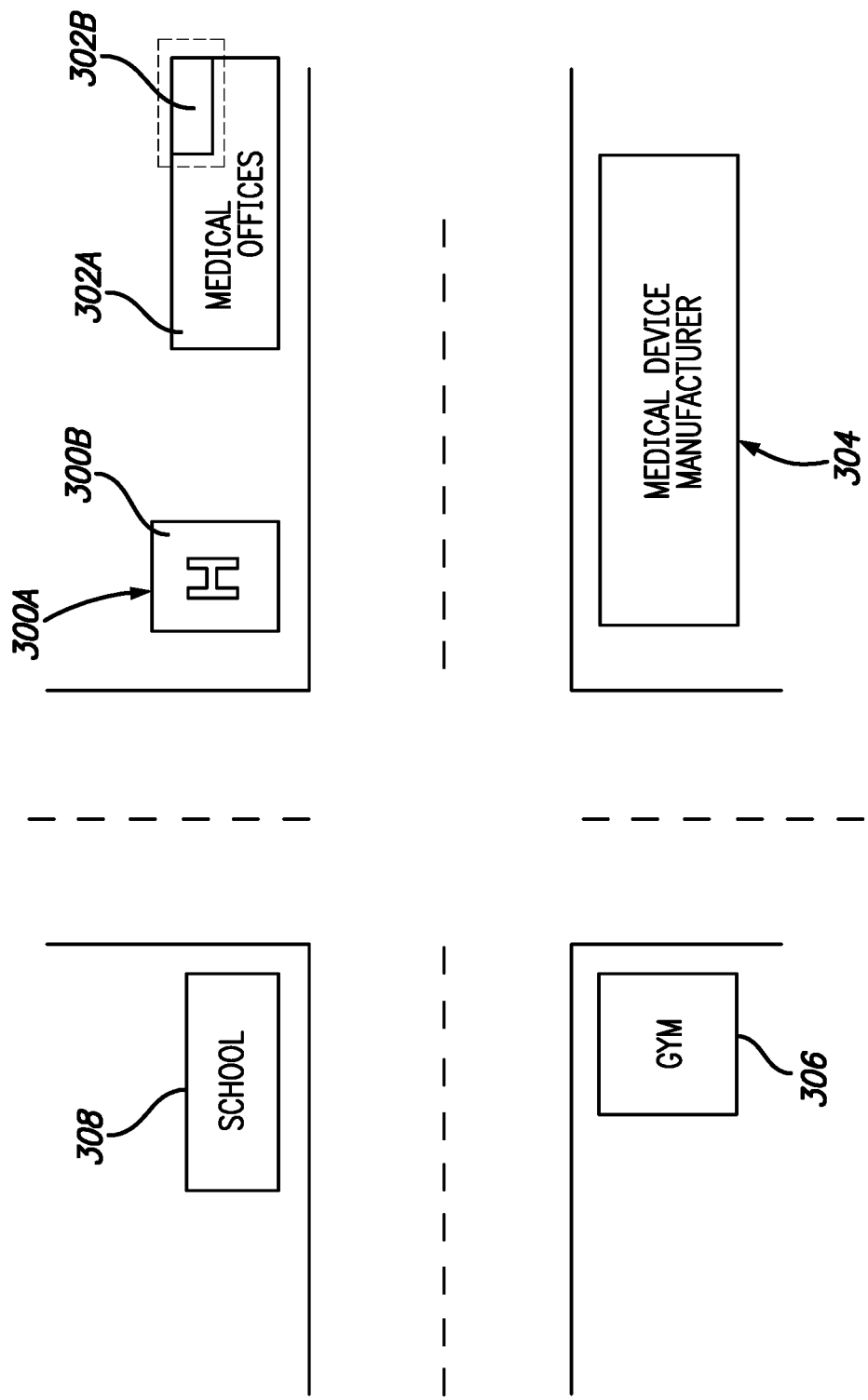

FIGS. 3A and 3B are exemplary illustrations of various locations or scenarios where inclusion of a GPS receiver could be used to enable or disable various features of the infusion pump, in accordance with embodiments of the present invention. FIGS. 3A and 3B illustrates various buildings or facilities where a GPS enabled infusion device could provide automatic or manually enabled enhanced capability for a user. In one embodiment medical offices 302A includes a suite 302B of exam rooms and offices designated by dotted line. Within suite 302B a clinical study utilizing the infusion pump can be conducted. Accordingly, the infusion pump can be programmed to enable access to programming specific to the clinical trial when the infusion pump or infusion pump and controller are within the safe zone as reported by the GPS receiver. Devices operating within the safe zone will be able to operate on unapproved or experimental protocols with the GPS enabled safeguard that if the device is removed from the safe zone, operation of the device will automatically revert to approved protocols. Thus, a GPS enabled infusion system can help mitigate any risk associated with potential misuse or accidental use of a clinical trial device outside of a specified protocol.

In embodiments where there infusion device incudes a GPS receiver the GPS coordinates received by the infusion device receiver will be used to determine if the system is within the safe zone. In embodiments where the infusion system includes a single GPS receiver associated with the controller loss it may become possible for the controller to be located outside of a safe zone while the infusion device is within the safe zone or vice versa. Thus, a user could potentially leave a controller within a safe zone in order to receive an experimental therapy and then wander away from the safe zone while the infusion device continues to deliver the experimental therapy. To prevent this some embodiments monitor communication between the controller and the infusion device. If the controller and infusion device become separated by too much distance the infusion device will automatically begin executing the first instruction set.

In another embodiment GPS coordinates for a gym 306 have been programmed into the infusion system in order to better tailor a user's therapy based on their environment. In embodiments where the infusion system is used to deliver insulin for diabetes therapy a user prone to low blood sugar may be forgetful in suspending basal insulin delivery when they exercise at the gym. With the GPS enabled infusion system upon entering the designated gym safe zone the infusion pump can automatically, or request user confirmation to suspend basal delivery until the GPS receiver detects the user as exited the gym safe zone. Upon leaving the safe zone the GPS enabled infusion system can automatically restart basal delivery. In other embodiments, departure from the safe zone creates an alarm condition that requests the user to verify resumption of basal delivery.

In still another embodiment, various functions of a device can be automatically disabled based on a user's location. An example where this feature may be implemented would be when devices are given to children or the elderly. When a user is within the safe zone of locations where proper supervision is available, such as a home, hospital 300 or physician's office 302, full functionality of the device may be enabled. Upon detecting the device is outside of the safe zones functionality of the device may be disabled to prevent accidental or purposeful manipulation of therapy. For example, when outside of a designated safe zone near their home a child's insulin system can be prevented from delivery boluses larger than a specified limit. This can be used to prevent the child from eating sugary snacks and junk food and attempting to hide the incident from their parents by delivering a large bolus. In another embodiment, if a safe zone is established around a school 308 attended by a child, some select features may be enabled with secondary authorization. This could enable trained teachers or administrators to access settings on the infusion device that would otherwise be locked out.

Another exemplary scenario where having a second set of operating instructions enabled when an integrated GPS receiver is located within a safe zone is the installation and verification of over the air software updates. Various design consideration can result in difficulty disassembling a device in order to access hardware based inputs to install software or firmware updates. For such devices over-the-air updates or remote software updates may be enabled but the risk of tampering or hacking wireless communication should be minimized. This risk can be partially mitigated by only allowing over-the-air updates to a device to be performed inside a safe zone associated with the GPS coordinates of a medical device manufacturer 304. In alternative embodiments a user can define a safe zone within their home that also allows over-the-air updates to software or firmware for the device to be installed. In some embodiments, to further ensure integrity of any updates upon entering the safe zone a user would be required to perform a secondary authentication before having to manually accept an over-the-air update.

Another feature enabled by an integrated GPS receiver is integrating GPS coordinates with restaurant or café locations to enable users to easily access nutritional information on either the controller or the infusion pump. In this embodiment it may not be necessary to enter a safe zone or load a second set of operating instructions for the infusion pump. Rather, simply by enabling GPS location reporting a dialog box or notification would be made on the display that would allow the user to access nutritional information specific to the establishment they entered or they are near. In some embodiments the user would be able to select items they wish to order from a graphical display of icons or a simple list that corresponds to items available from the restaurant/café. In embodiments specific to diabetes therapy, a total number of carbohydrates contained in the selected items would be displayed along with optional suggestions of alternate menu items more in line with a user's therapy. If satisfied with the selected items, the user can directly program a bolus to be delivered without having to guess or estimate the carbohydrates to be consumed.

Figure 4:
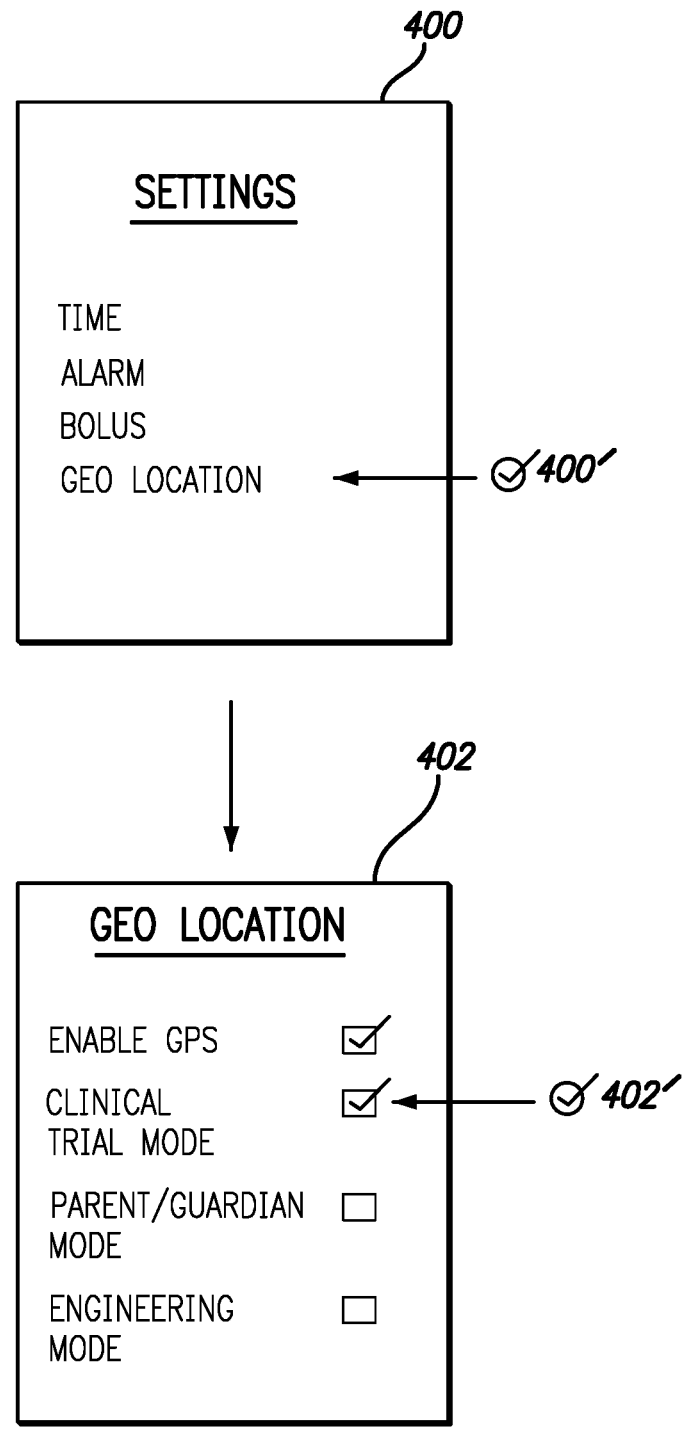
FIG. 4 are exemplary screenshots to illustrate entering and programming GPS enabled features, in accordance with one embodiment of the present invention.

FIG. 4 includes exemplary screenshots to illustrate entering and programming GPS enabled features, in accordance with one embodiment of the present invention. Screen 400 is an exemplary display showing types of SETTINGS that can be configured. Checkmark 400' and corresponding arrow indicates the menu item on the screen 400 that is selected using the user interface. For example, 400' indicates that GEO LOCATION is selected from the SETTINGS screen.

Screen 402 is one embodiment of GEO LOCATION settings that can be configured by a user. Checkmark 402' and corresponding arrow show CLINICAL TRIAL MODE being selected via the user interface. In most embodiments secondary authentication will be required before clinical trial software can be loaded into the infusion pump memory. In some embodiments the secondary authentication may require registration of a pump serial number with a secure database associated with the clinical trial. The clinical trial database can return a single user authenticated ID and password that is associated with the infusion pump serial number. Additionally, clinical trial software to be loaded onto the infusion device can be generated that is keyed to be unlocked using the authenticated ID, password and pump serial number. In other embodiments various other forms of secondary authentication can be used to limit access to the clinical trial software. The clinical trial software loaded into the infusion pump may include predefined safe zones. In other embodiments, safe zones may be user defined based on the type of control being enabled or disabled on the infusion pump.

In other embodiments upon proper authentication a user may establish various safe zones around specified GPS coordinates. In embodiments where the controller or infusion device includes internet access a user can enter a street address that can be resolved to GPS coordinates and then specify the safe zone around the resolved GPS coordinates. In many embodiments the safe zone is a distance measures in feet, meters, yards and the like. Upon entry of the safe zone the display can show an approximate area covered by the safe zone on a map. In some embodiments the map will also show the safe zone and additionally show a GPS accuracy zone that is attributable to the precision of the GPS system approximately 7.8 meters outside the specified GPS coordinates.

Figure 5:
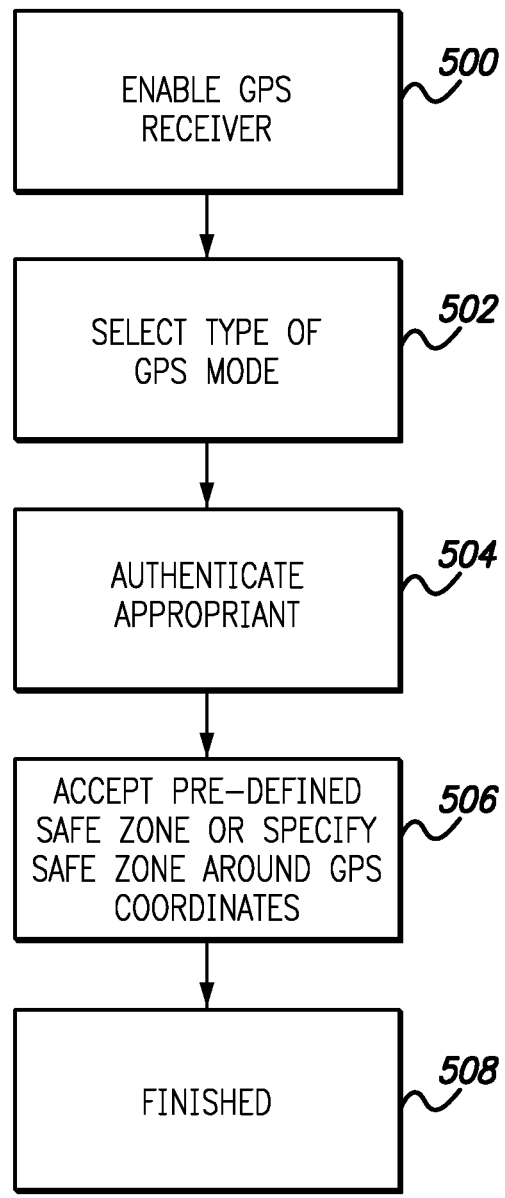
FIG. 5 is a flow chart illustrating exemplary operation of a GPS enabled infusion system, in accordance with embodiments of the present invention.

FIG. 5 is a flow chart illustrating exemplary operation of a GPS enabled infusion system, in accordance with embodiments of the present invention. The flow chart begins with operation 500 where a user enables the GPS receiver. For devices where a single GPS receiver is found on a controller that is a mobile device such as a mobile smartphone and the infusion pump does not include a GPS receiver, this operation enables the smartphone to share GPS data with an infusion pump controller application concurrently running on the smartphone. Operation 502 allows a user to select a type of GPS mode. In one embodiment, various GPS modes are allowed such as, but not limited to Clinical Trial mode, Parent or Guardian mode, and Engineering mode. Because the various modes may allow access and customization of various levels of hardware and software, operation 504 requires appropriate authentication. In one embodiment, the more hardware and software operations that are accessible to be modified, the more secure the authentication process. For example, setting maximum bolus levels or locking out particular menu selections can be enabled in Parent or Guardian mode. Access at this level can require a parent or guardian to enter a password or passcode in order to modify the settings within Parent/Guardian mode. In both Clinical Trial mode and Engineering mode, therapies and protocols may be modified thereby requiring increased levels of security. Access to these modes may require two-phase authentication along with other enhanced security measures.

Once authentication is completed operation 506 enables a user to either define GPS coordinates and associated user defined safe zones or load clinical trial or experimental engineering program instructions that include defined safe zones for specified GPS coordinates. With operation 506 a user can define a safe zone around the GPS coordinates at the center of their home. This can enable full functionality of the infusion pump within the defined safe zone and further define limited functionality outside of the safe zone. For clinical trials this enables program instructions to be loaded into memory of the infusion pump that define a safe zone around GPS coordinates associated with the clinical trial. In embodiments where the safe zone is user defined it can be input in various dimensions such as feet, meters, yards and the like from specified GPS coordinates. Having enabled GPS location for the infusion pump operation 508 completes the flow chart.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion system comprising:
an infusion pump;
a global positioning system (GPS) receiver; and
a processor configured to execute instructions stored in a memory comprising:
determining a location of the infusion pump via GPS coordinates;
determining whether the location of the infusion pump is within a safe zone defined around specified GPS coordinates, wherein the safe zone is a measured distance around the specified GPS coordinates; and
enabling or disabling one or more functions of the infusion system based on the determining of whether the location of the infusion pump is within the safe zone.

2. The infusion system of claim 1, further comprising a sensor set that provides continuous data of sensor readings to the infusion system.

3. The infusion system of claim 1, further comprising a controller having a user interface and the GPS receiver integrated therein, wherein the controller controls the infusion pump having minimal or no user interface.

4. The infusion system of claim 1, wherein the infusion pump itself includes the GPS receiver and a user interface.

5. The infusion system of claim 1, further comprising a controller wherein both the controller and the infusion pump each include a GPS receiver and a user interface.

6. The infusion system of claim 1, wherein the processor is configured to execute further instructions comprising causing the infusion system to send a prompt for a user to manually activate the one or more functions enabled based on a determination that the location of the infusion pump is within the safe zone.

7. The infusion system of claim 1, wherein the measured distance around the specified GPS coordinates is measured in at least one of feet, meters, or yards.

8. A system comprising:
an infusion pump including a processor, a memory and a sensor suite,
wherein the sensor suite includes a global positioning system (GPS) receiver that determines GPS coordinates of the infusion pump,
wherein the GPS receiver is coupled to the processor that executes first instructions stored in the memory, and wherein the processor executes second instructions stored in the memory in response to determining that the location of the infusion pump is within a safe zone defined around specified GPS coordinates, wherein the safe zone is a measured distance around the specified GPS coordinates.

9. The system of claim 8, further comprising:
a controller for the infusion pump, the controller having a controller processor, controller memory, controller communication suite and controller user interface, the controller communication suite enabling a bi-directional interface between the controller and the infusion pump, the bi-directional interface enabling the controller to modify programming of the infusion pump.

10. The system of claim 8, wherein the first instructions correspond to an approved therapy and the second instructions correspond to a trial therapy.

11. The system of claim 8, wherein if GPS coordinates are unavailable, the infusion pump automatically executes the first instructions.

12. The system of claim 8, wherein storing the second instructions in the memory requires secondary authentication.

13. The system of claim 8, wherein the first instructions disable software updates to the infusion pump and the second instructions enable software updates to the infusion pump.

14. A method for a global positioning system (GPS) enabled infusion system, the method comprising:
determining, electronically by a processor of the GPS enabled infusion system, a location of an infusion pump via a GPS receiver;
determining, electronically by the processor, whether the location of the infusion pump is within a safe zone defined around specified GPS coordinates, wherein the safe zone is a measured distance around the specified GPS coordinates; and
enabling or disabling one or more functions of the GPS enabled infusion system based on the determination of whether the location of the infusion pump is within the safe zone.

15. The method of claim 14, further comprising providing, electronically by the processor, a selection of types of GPS modes.

16. The method of claim 15, wherein the providing the selection further comprises providing a selection of at least one of a clinical trial mode, a parent or guardian mode, or an engineering mode.

17. The method of claim 15, further comprising requiring appropriate authentication for accessing the types of GPS modes.

18. The method of claim 14, further comprising enabling a user to define the specified GPS coordinates and associated user defined safe zones.

19. The method of claim 18, enabling the user to define the safe zone in one or more dimensions including at least one of feet, meters, or yards, from the specified GPS coordinates.

20. The method of claim 14, further comprising enabling a user to load instructions that include defined safe zones for specified GPS coordinates.

* * * * *